(12) United States Patent
Nakamura

(10) Patent No.: US 8,876,721 B2
(45) Date of Patent: Nov. 4, 2014

(54) ULTRASOUND DIAGNOSTIC APPARATUS

(75) Inventor: Kenji Nakamura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 359 days.

(21) Appl. No.: 13/353,006

(22) Filed: Jan. 18, 2012

(65) Prior Publication Data

US 2012/0197124 A1 Aug. 2, 2012

(30) Foreign Application Priority Data

| Feb. 1, 2011 | (JP) | ................................ 2011-019576 |
| Feb. 1, 2011 | (JP) | ................................ 2011-019694 |
| Feb. 9, 2011 | (JP) | ................................ 2011-025969 |
| Feb. 9, 2011 | (JP) | ................................ 2011-025986 |

(51) Int. Cl.
*A61B 8/00* (2006.01)

(52) U.S. Cl.
CPC ... *A61B 8/56* (2013.01); *A61B 8/42* (2013.01); *A61B 8/4472* (2013.01)
USPC ....................................................... 600/459

(58) Field of Classification Search
CPC ............................................................ A61B 8/56
USPC ........................................................ 600/459
See application file for complete search history.

(56) References Cited

U.S. PATENT DOCUMENTS

| 5,660,554 | A * | 8/1997 | Mead ............................. 439/172 |
| 6,117,085 | A | 9/2000 | Picatti et al. |
| 7,626,327 | B2 | 12/2009 | Shimada et al. |
| 2004/0015079 | A1 * | 1/2004 | Berger et al. ................. 600/437 |
| 2006/0100513 | A1 | 5/2006 | Hashimoto |
| 2007/0282383 | A1 | 12/2007 | Koyama |
| 2010/0160785 | A1 | 6/2010 | Poland et al. |
| 2010/0185096 | A1 | 7/2010 | Miyachi et al. |
| 2010/0298711 | A1 * | 11/2010 | Pedersen et al. .............. 600/459 |
| 2011/0208068 | A1 | 8/2011 | Ariga et al. |
| 2012/0006994 | A1 | 1/2012 | Niekawa et al. |

FOREIGN PATENT DOCUMENTS

| JP | 11-244237 | 9/1999 |
| JP | 2000-271141 | 10/2000 |
| JP | 2001-017385 | 1/2001 |
| JP | 2002-530175 | 9/2002 |

(Continued)

OTHER PUBLICATIONS

Japanese Office Action dated Dec. 11, 2012 in corresponding Japanese Patent Application No. 2011-025986 with English translation of Japanese Office Action.

(Continued)

*Primary Examiner* — Jonathan Cwern
(74) *Attorney, Agent, or Firm* — Young & Thompson

(57) ABSTRACT

An ultrasound diagnostic apparatus comprises: an ultrasound probe that has a transducer array transmitting an ultrasonic beam toward a subject and receiving an ultrasonic echo by the subject to output reception signals; a diagnostic apparatus body that is connected to the ultrasound probe by wireless communication and generates an ultrasound image on the basis of the reception signal output from the transducer array; at least one power receiving terminal that is arranged at the ultrasound probe and electrically connected to respective parts in the ultrasound probe; and a power supply unit that is capable of being attached to an operator's body and is detachably connected to the power receiving terminal so as to perform power supply to the respective parts in the ultrasound probe.

5 Claims, 11 Drawing Sheets

(56) References Cited

FOREIGN PATENT DOCUMENTS

| | | |
|---|---|---|
| JP | 2003-010177 | 1/2003 |
| JP | 2005-279255 | 10/2005 |
| JP | 2006-158411 | 6/2006 |
| JP | 2007-028537 | 2/2007 |
| JP | 2007-275088 | 10/2007 |
| JP | 2008-006275 | 1/2008 |
| JP | 2008-131812 | 6/2008 |
| JP | 2010-110379 | 5/2010 |
| JP | 2010-167083 | 8/2010 |
| JP | 2010-179052 | 8/2010 |
| JP | 2010-528698 | 8/2010 |
| JP | 2010-233826 | 10/2010 |
| WO | WO 2010/109984 | 9/2010 |

OTHER PUBLICATIONS

Notification of Reasons for Refusal mailed Jan. 8, 2013 by the Japanese Patent Office in corresponding Japanese Patent Application No. 2011-019576 with partial translation, 6 pages.

Notification of Reasons for Refusal mailed Jan. 8, 2013 by the Japanese Patent Office in corresponding Japanese Patent Application No. 2011-025969 with partial translation, 6 pages.

* cited by examiner

ULTRASOUND DIAGNOSTIC APPARATUS

CROSS-REFERENCE TO RELATED APPLICATIONS

The present application claims priority under 35 U.S.C. §119 to Japanese Patent Applications No. 2011-019694, filed Feb. 1, 2011, No. 2011-019576, filed Feb. 1, 2011, No. 2011-025969, filed Feb. 9, 2011, and No. 2011-025986, filed Feb. 9, 2011. Each of the above applications is hereby expressly incorporated by reference, in its entirety, into the present application.

BACKGROUND OF THE INVENTION

The present invention relates to an ultrasound diagnostic apparatus, and particularly, to a power supply method to an ultrasound probe of an ultrasound diagnostic apparatus that performs diagnosis on the basis of an ultrasound image generated by transmitting and receiving ultrasonic waves from a transducer array of the ultrasound probe.

The present invention also relates to measures against heat dissipation of the ultrasound probe.

In the related art, ultrasound diagnostic apparatuses using an ultrasound image are being put into practical use in the medical field. Generally, this type of ultrasound diagnostic apparatus has an ultrasound probe with a built-in transducer array, and an apparatus body connected to this ultrasound probe. Ultrasonic waves are transmitted toward a subject from the ultrasound probe, and the ultrasound probe receives ultrasonic echoes from the subject and generates an ultrasound image by electrically processing reception signals in the apparatus body.

In recent years, in order to eliminate the problems with a communication cable that connects the ultrasound probe and the apparatus body together and thereby improve operativity, an ultrasound diagnostic apparatus that connects an ultrasound probe and an apparatus body by wireless communication is being developed.

In such a wireless communication type ultrasound diagnostic apparatus, generally, a rechargeable battery is contained within the ultrasound probe as a power source, and when charging of the battery is required, for example, as in the apparatus described in JP 2002-530175 A, power is fed from a power supply part of the apparatus body to the battery in the ultrasound probe in a state where the ultrasound probe is housed in a probe holder set in the apparatus body, and an external charge contact of the ultrasound probe is connected to a contact on the side of the probe holder, or as in apparatuses described in JP 2010-233826 A and JP 2010-167083 A, power is fed to the battery in a non-contact manner by electromagnetic induction or the like from a power supply part of a power supply apparatus set around the diagnostic apparatus body or diagnostic apparatus.

However, in the apparatus of JP 2002-530175 A, in order to house the ultrasound probe in the probe holder of the apparatus body to charge the battery, there is a concern that ultrasonic diagnosis may need to be suspended when this battery is charged, and the ultrasonic diagnosis may be hindered. In the apparatus of JP 2010-233826 A, there is a concern that the distance between the power supply part set around the diagnostic apparatus and the power receiving part of the ultrasound probe may change according to an operator's standing position, or that it may become impossible to efficiently supply electric power to the ultrasound probe due to the influence of electronic devices or the like around the ultrasound diagnostic apparatus.

Additionally, the continuous running time of an ultrasound probe with a built-in battery is influenced by the capacity of the battery, and the exhaustion speed of the battery. Thus, in the apparatus described in JP 2010-167083 A, in order to enable prolonged continuous running, the amount of electric power remaining in the battery is checked. When the amount of electric power remaining is equal to or less than a threshold, a non-power-saving mode in which priority is given to the image quality of an ultrasound image is changed to a power-saving mode in which priority is given to the functions of the probe and the apparatus body, and the electric power to be supplied to the probe and the apparatus body is limited by the power-saving mode, thereby suppressing the consumption of the electric power of the battery.

However, in the apparatus of JP 2010-167083 A, if the electric power of the battery built in the ultrasound probe becomes equal to or less than a predetermined quantity even if the consumption of the electric power of the battery is suppressed by appropriately changing the non-power-saving mode in which priority is given to the image quality of an ultrasound image to the power-saving mode in which priority is given to apparatus functions, in order to replace the existing battery with a new battery or to set the existing batter at the diagnostic apparatus body to supply electric power to the ultrasound probe, there is a concern that the use of the ultrasound probe may be temporarily suspended. Additionally, even if an operator desires a high image-quality ultrasound image as being obtained in the non-power-saving mode during diagnosis in the power-saving mode, it is difficult to make a change to the non-power-saving mode from the balance with the exhaustion of the battery.

Additionally, the related-art ultrasound diagnostic apparatuses have also a problem regarding the generation of heat by the ultrasound probe.

In general ultrasound diagnostic apparatuses that transmit and receive ultrasonic waves from the transducer array of the ultrasound probe, thereby generating an ultrasound image, heat is generated from the transducer array as ultrasonic waves from the transducer array are transmitted. However, normally, since diagnosis is performed while an operator grips the ultrasound probe with one hand and brings an ultrasound transmission/reception surface of the transducer array into contact with the surface of a subject, the ultrasound probe is often accommodated in a small housing such that the operator may easily grip the probe with one hand. For this reason, the temperature in the housing of the ultrasound probe may rise due to the generation of heat from the transducer array.

Additionally, in recent years, there has been proposed an ultrasound diagnostic apparatus that reduces the influence of noise to obtain a high image-quality ultrasound image by building a circuit board for signal processing in the ultrasound probe, and transmitting reception signals output from the transducer array to the apparatus body by wireless communication or cable communication after being subjected to digital processing. In the ultrasound probe that performs this kind of digital processing, heat is generated from the circuit board even when the processing of the reception signals is performed, and in order to guarantee a stable operation of each circuit of the circuit board, it is necessary to suppress a temperature rise in the housing.

Thus, for example, JP 2006-158411 A discloses an ultrasound diagnostic apparatus configured so as to cool the ultrasound probe, using a cooling medium, such as water. A cooling medium circulation unit is mounted on a probe connector part that forms a cooling medium pipe along a cable connecting the diagnostic apparatus body and the ultrasound probe, and connects this cable to the diagnostic apparatus body, and a cooling medium is circulated between the probe connector part of the diagnostic apparatus body, and the ultrasound probe via the cooling medium pipe by the circulation unit, whereby cooling of the ultrasound probe is performed. However, in such an apparatus, there is a problem in that the cooling medium circulation unit needs to be mounted on the probe connector part of the diagnostic apparatus body, and the ultrasound diagnostic apparatus is complicated. Additionally, since the cooling medium pipe is formed along the cable that connects the diagnostic apparatus body and the ultrasound probe, the diameter of the cable increases and the flexibility of the cable deteriorates, and therefore, there is a concern that the operativity that is an important performance for the ultrasound probe may be adversely affected.

SUMMARY OF THE INVENTION

The invention has been made in order to solve such related-art problems, and an object thereof is to provide an ultrasound diagnostic apparatus that can continue ultrasonic diagnosis for a prolonged period of time, without damaging the operativity of an ultrasound probe.

Additionally, another object of the invention is to provide an ultrasound diagnostic apparatus that can also acquire a high image-quality ultrasound image if required for diagnosis.

Moreover, still another object of the invention is to provide an ultrasound diagnostic apparatus that has a simple structure, and can perform heat dissipation of the ultrasound probe without damaging the operativity of the ultrasound probe.

An ultrasound diagnostic apparatus according to a first aspect of the present invention comprises:

an ultrasound probe that has a transducer array transmitting an ultrasonic beam toward a subject and receiving an ultrasonic echo by the subject to output reception signals;

a diagnostic apparatus body that is connected to the ultrasound probe by wireless communication and generates an ultrasound image on the basis of the reception signals output from the transducer array;

at least one power receiving terminal that is arranged at the ultrasound probe and electrically connected to respective parts in the ultrasound probe; and a power supply unit that is capable of being attached to an operator's body and is detachably connected to the power receiving terminal so as to perform power supply to the respective parts in the ultrasound probe.

An ultrasound diagnostic apparatus according to a second aspect of the present invention comprises:

an ultrasound probe that has a transducer array transmitting an ultrasonic beam toward a subject and receiving an ultrasonic echo by the subject to output reception signals;

a diagnostic apparatus body that generates an ultrasound image on the basis of the reception signals output from the transducer array;

at least one heat dissipation terminal that is arranged at the ultrasound probe and thermally connected to heat generating parts in the ultrasound probe; and a heat dissipation unit that is capable of being attached to an operator's body and is detachably connected to the heat dissipation terminal so as to release the heat generated in the heat generating parts in the ultrasound probe.

An ultrasound diagnostic apparatus according to a third aspect of the present invention comprises:

an ultrasound probe that has a transducer array transmitting an ultrasonic beam toward a subject and receiving an ultrasonic echo by the subject to output reception signals;

a diagnostic apparatus body that is connected to the ultrasound probe by wireless communication and generates an ultrasound image on the basis of the reception signals output from the transducer array;

a wireless power receiving part that is arranged at the ultrasound probe and electrically connected to respective parts in the ultrasound probe; and a power supply unit capable of being attached to an operator's body, and having at least one wireless power supply part wirelessly connected to the wireless power receiving part of the ultrasound probe so as to perform power supply to the respective parts in the ultrasound probe.

An ultrasound diagnostic apparatus according to a fourth aspect of the present invention comprises:

an ultrasound probe that has a transducer array transmitting an ultrasonic beam toward a subject and receiving an ultrasonic echo by the subject to output reception signals;

a diagnostic apparatus body that is connected to the ultrasound probe by wireless communication and generates an ultrasound image on the basis of the reception signals output from the transducer array;

a wireless power receiving part that is arranged at the ultrasound probe and electrically connected to respective parts in the ultrasound probe;

a power supply unit having a wireless power supply part wirelessly connected to the wireless power receiving part of the ultrasound probe so as to perform power supply to the respective parts in the ultrasound probe;

a selector that selects either of a first mode in which transmission and reception of ultrasonic waves are performed by the transducer array of the ultrasound probe while performing power supply by the wireless power supply part, and a second mode in which power supply is stopped by the wireless power supply part to perform the transmission and reception of an ultrasonic wave by the transducer array of the ultrasound probe; and a controller that controls the power supply by the wireless power supply part and the transmission and reception of the ultrasonic wave by the transducer array of the ultrasound probe on the basis of the mode selected from the first mode and the second mode by the selector.

DETAILED DESCRIPTION OF THE INVENTION

Embodiments of the invention will be described below with reference to the accompanying drawings.

Embodiment 1

Figure 1:
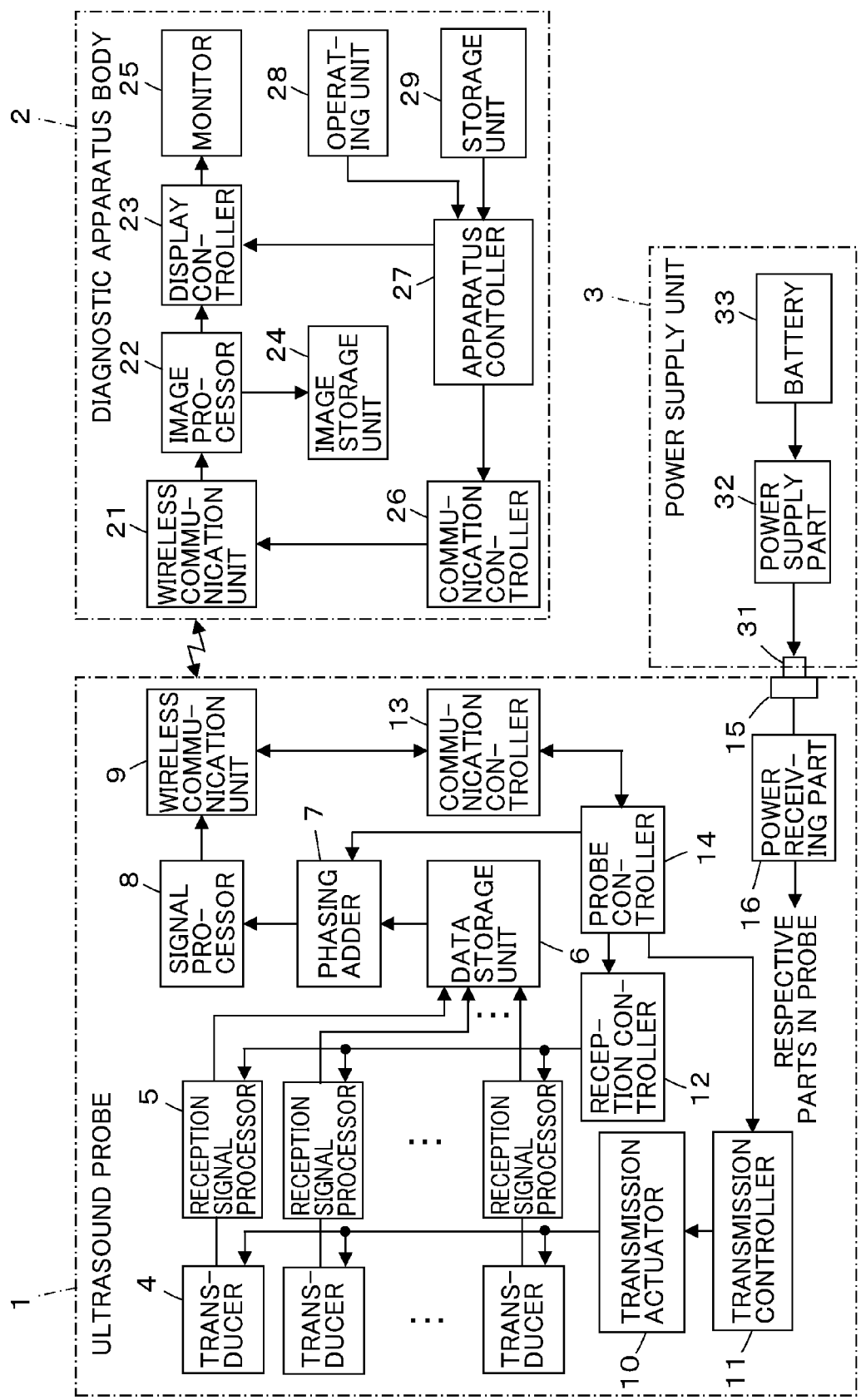
FIG. 1 is a block diagram showing the configuration of an ultrasound diagnostic apparatus related to Embodiment 1 of the invention.

FIG. 1 shows the configuration of an ultrasound diagnostic apparatus related to Embodiment 1 of the invention. The ultrasound diagnostic apparatus includes an ultrasound probe 1, a diagnostic apparatus body 2 connected to the ultrasound probe 1 by wireless communication, and a power supply unit 3 detachably connected to the ultrasound probe 1.

The ultrasound probe 1 has a plurality of ultrasound transducers 4 that constitute a plurality of channels for a one-dimensional or two-dimensional transducer array, reception signal processors 5 are connected to the transducers 4 so as to correspond to the transducers, respectively, and a wireless communication unit 9 is connected to the reception signal processors 5 via a data storage unit 6, a phasing adder 7, and a signal processor 8 sequentially. Additionally, a transmission controller 11 is connected to the plurality of transducers 4 via a transmission actuator 10, a reception controller 12 is connected to the plurality of reception signal processors 5, and a communication controller 13 is connected to the wireless communication unit 9. A probe controller 14 is connected to the transmission controller 11, the reception controller 12, and the communication controller 13. Moreover, the ultrasound probe 1 includes a power receiving terminal 15 attached to a housing, and a power receiving part 16 connected to the power receiving terminal 15 and electrically connected to respective parts that require electric power in the ultrasound probe 1.

The plurality of transducers 4 transmits ultrasonic waves according to actuation signals supplied from the transmission actuator 10, respectively, and receives ultrasonic echoes from a subject to output reception signals. Each transducer 4 is constituted by a piezoelectric body made of, for example, piezoelectric ceramics represented by PZT (lead zirconate titanate), a polymer piezoelectric device represented by PVDF (polyvinylidene fluoride), or the like, and electrodes provided at both ends of the piezoelectric body.

If a pulsed or continuous-wave voltage is applied to the electrodes of such transducers 4, the piezoelectric bodies expand and contract, pulsed or continuous-wave ultrasonic waves are generated from the respective transducers 4, and an ultrasonic beam is formed by the synthesis of the ultrasonic waves. Additionally, the respective transducers 4 receive ultrasonic waves to be propagated, thereby expanding and contracting to generate electrical signals, and the electrical signals are output as reception signals of the ultrasonic waves.

The transmission actuator 10 includes, for example, a plurality of pulsars, and regulates the delay amounts of the respective actuation signals to supply the delay amounts to the plurality of transducers 4 such that the ultrasonic waves transmitted from the plurality of transducers 4 form a broad ultrasonic beam that covers the area of a tissue in a subject, on the basis of a transmission delay pattern selected by the transmission controller 11.

Under the control of the reception controller 12, the reception signal processor 5 of each channel performs orthogonal detection processing or orthogonal sampling processing on the reception signal output from a corresponding transducer 4, thereby generating a complex baseband signal, and samples the complex baseband signal, thereby generating sample data including information on the area of the tissue. The reception signal processor 5 may perform data compression processing for high-efficiency coding on the data obtained by sampling the complex baseband signal, thereby generating the sample data.

The data storage unit 6 is constituted by a memory or the like and stores the sample data equivalent to at least one frame generated in the plurality of reception signal processors 5.

The phasing adder 7 selects one reception delay pattern from a plurality of reception delay patterns stored in advance, according to a reception direction set in the probe controller 14, and gives and adds respective delays to a plurality of complex baseband signals expressed by the sample data, on the basis of the selected reception delay pattern, thereby performing reception focusing processing. Baseband signals (sound ray signals) in which the focal points of ultrasonic echoes are narrowed are generated by this reception focusing processing.

The signal processor 8 performs the correction of attenuation based on a distance, on the sound ray signals generated by the phasing adder 7, according to the depth of the reflection positions of the ultrasonic waves, and converts (raster-convert) the sound ray signals into image signals according to a scan mode of normal television signals, thereby generating B mode image signals that are tomographic image information regarding a tissue in a subject.

The wireless communication unit 9 modulates carriers to generate transmission signals, on the basis of the B mode image signals generated in the signal processor 8, and supplies the transmission signals to an antenna and transmits radio waves from the antenna, thereby transmitting the B mode image signals. As modulation methods, for example, ASK (Amplitude Shift Keying), PSK (Phase Shift Keying), QPSK (Quadrature Phase Shift Keying), 16QAM (16 Quadrature Amplitude Modulation), and the like are used.

The wireless communication unit 9 performs wireless communication with the diagnostic apparatus body 2, thereby transmitting the B mode image signals to the diagnostic apparatus body 2, and receives various control signals from the diagnostic apparatus body 2, to output the received control signals to the communication controller 13. The communication controller 13 controls the wireless communication unit 9 such that the transmission of the B mode image signals is performed with a transmission radio field intensity set by the probe controller 14, and outputs the various control signals that the wireless communication unit 9 has received to the probe controller 14.

The probe controller 14 controls the respective parts of the ultrasound probe 1, on the basis of the various control signals transmitted from the diagnostic apparatus body 2.

The power receiving part 16 connected to the power receiving terminal 15 is provided to supply electric power to respective parts that require electric power in the ultrasound probe 1.

In addition, the ultrasound probe 1 may be an external type probe using a linear scanning method, a convex scanning method, a sector scanning method, and the like, or may be a probe for an ultrasound endoscopy, using a radial scanning method, and the like.

On the other hand, the diagnostic apparatus body 2 has a wireless communication unit 21, an image processor 22 is connected to the wireless communication unit 21, a display controller 23 and an image storage unit 24 are connected to the image processor 22, respectively, and a monitor 25 is connected to the display controller 23. Additionally, a communication controller 26 is connected to the wireless communication unit 21, and an apparatus controller 27 is connected to the display controller 23 and the communication controller 26. Moreover, an operating unit 28 that allows an operator to perform input operations and the storage unit 29 that stores an operation program and the like are connected to the apparatus controller 27, respectively.

The wireless communication unit 21 performs wireless communication with the ultrasound probe 1, thereby transmitting the various control signals to the ultrasound probe 1. Additionally, the wireless communication unit 21 demodulates the signals received by the antenna, thereby outputting the B mode image signals.

The communication controller 26 controls the wireless communication unit 21 such that the transmission of the various control signals is performed with the transmission radio field intensity set by the apparatus controller 27.

The image processor 22 performs various kinds of required image processing, such as gradation processing, on the B mode image signals input from the communication controller 26, and then, outputs the B mode image signals to the display controller 23 or stores these signals in the image storage unit 24.

The display controller 23 displays an ultrasound diagnostic image on the monitor 25, on the basis of the B mode image signals subjected to the image processing by the image processor 22. The monitor 25 includes a display unit, such as an LCD, and displays the ultrasound diagnostic image under the control of the display controller 23.

In such a diagnostic apparatus body 2, the image processor 22, the display controller 23, the communication controller 26, and the apparatus controller 27 are constituted by a CPU and operation programs for making the CPU perform various kinds of processing. However, these processor and controllers may be constituted by a digital circuit. The above operation programs are stored in the storage unit 29. As a recording medium in the storage unit 29, a flexible disk, an MO, an MT, a RAM, a CD-ROM, a DVD-ROM or the like other than a built-in hard disk can be used.

The power supply unit 3 is provided to supply electric power to the ultrasound probe 1, and further includes a power supply terminal 31 detachably connected to the power receiving terminal 15 of the ultrasound probe 1, a power supply part 32 electrically connected to the power supply terminal 31, and a battery 33 electrically connected to the power supply part 32.

The power supply part 32 is provided to supply the electric power from the battery 33 to the power receiving part 16 of the ultrasound probe 1 via the power supply terminal 31 and the power receiving terminal 15 of the ultrasound probe 1.

Figure 2:
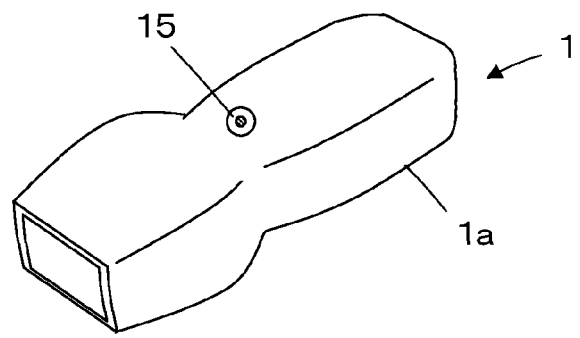
FIG. 2 is a perspective view showing an ultrasound probe in Embodiment 1.

As shown in FIG. 2, the power receiving terminal 15 is disposed at a housing 1a of the ultrasound probe 1 so as to be exposed to the outside.

Figure 3:
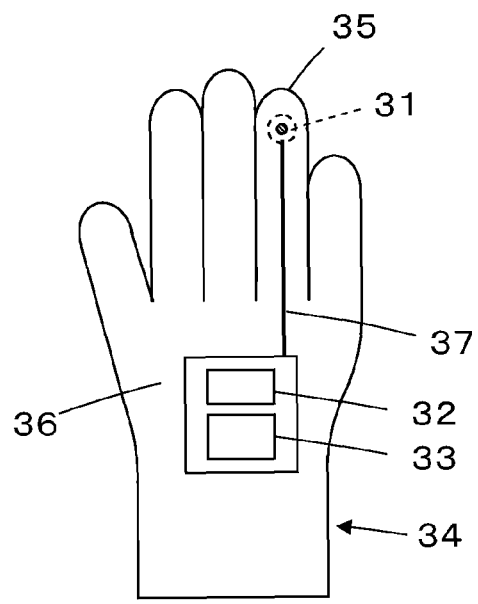
FIG. 3 is a view showing a glove to which a power supply unit is attached in Embodiment 1.

On the other hand, as shown in FIG. 3, the power supply unit 3 is attached to a glove 34 worn on an operator's hand. For example, the power supply terminal 31 is formed on the ventral side of a finger part 35 of the glove 34 so as to protrude therefrom, the power supply part 32 and the battery 33 are mounted on a back part 36 of the glove 34, and the power supply terminal 31 and the power supply part 32 are connected together via a conductive member 37.

Next, the operation of Embodiment 1 will be described.

Figure 4:
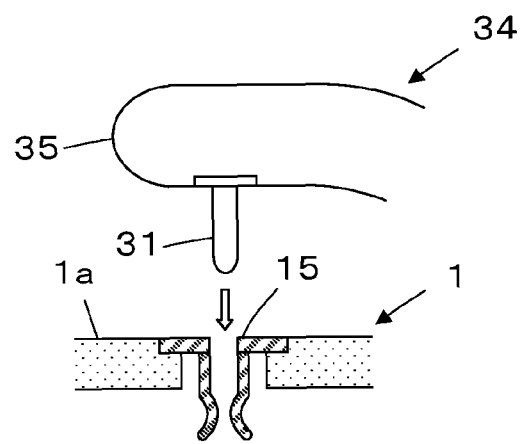
FIG. 4 is a view showing a power receiving terminal and a power supply terminal in Embodiment 1.

First, as shown in FIG. 4, an operator wears the glove 34 on his/her hand, and grips the housing 1a of the ultrasound probe 1 in a state where the power supply terminal 31 formed on the finger part 35 of the glove 34 so as to protrude therefrom is pressed against and fitted to the power receiving terminal 15 of the ultrasound probe 1, whereby the power supply terminal 31 and the power receiving terminal 15 are connected to each other. Thereby, the electric power from the battery 33 in the power supply unit 3 is supplied to the respective parts in the ultrasound probe 1 via the power supply part 32, the power supply terminal 31, and the power receiving terminal 15 and power receiving part 16 of the ultrasound probe 1.

Diagnosis is started in this state. That is, ultrasonic waves are transmitted from the plurality of transducers 4 that constitutes the transducer array according to actuation signals supplied from the transmission actuator 10 of the ultrasound probe 1, reception signals output from the respective transducers 4 that have received ultrasonic echoes from a subject are supplied to the corresponding reception signal processors 5, respectively, to generate sample data, sound ray signals are generated in the phasing adder 7, and then, B mode image signals generated in the signal processor 8 are wirelessly transmitted to the diagnostic apparatus body 2 from the wireless communication unit 9. The B mode image signals received in the wireless communication unit 21 of the diagnostic apparatus body 2 are subjected to image processing, such as gradation processing, in the image processor 22, and then, an ultrasound diagnostic image is displayed on the monitor 25 by the display controller 23, on the basis of the B mode image signals.

By connecting the power supply terminal 31 of the power supply unit 3 attached to the glove 34 worn on an operator's hand to the power receiving terminal 15 of the ultrasound probe 1 in this way, electric power can be supplied to the respective parts in the ultrasound probe 1 from the power supply unit 3. For this reason, it is not necessary to house the ultrasound probe in the probe holder of the diagnostic apparatus body and charge the battery built in the ultrasound probe, as in the related art, and it is possible to continue ultrasonic diagnosis for a prolonged period of time without damaging the operativity of the ultrasound probe 1.

In addition, the power supply terminal 31 is preferably arranged at the finger part 35, such as the ring finger and little finger of the glove 34, or can also be arranged on the palm of the glove 34 so that the operation of the ultrasound probe 1 is not damaged. Additionally, it is preferable to select the arrangement position of the power receiving terminal 15 in the housing 1a of the ultrasound probe 1 so that an operator may easily grip the ultrasound probe 1 according to the arrangement position of the power supply terminal 31 in the glove 34.

Although the power receiving terminal 15 is disposed at the housing 1a of the ultrasound probe 1 so as to be exposed to the outside, when an openable and closable lid is formed so as not to connect the power supply terminal 31 of the glove 34, the power receiving terminal can also be configured so as not to be touched by an operator's hand or finger from the outside. If such a lid is formed, a possibility that the power receiving terminal 15 may be damaged due to dust or the like is reduced.

Embodiment 2

Figure 5:
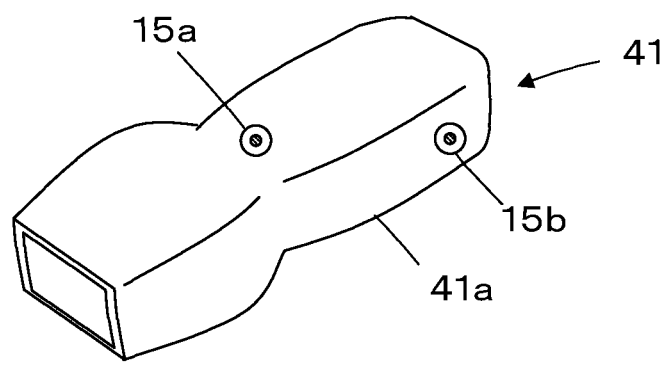
FIG. 5 is a perspective view showing an ultrasound probe in Embodiment 2.

FIG. 5 shows an ultrasound probe 41 related to Embodiment 2. The ultrasound probe 41 has a plurality of power receiving terminals 15a, 15b, etc. at mutually different positions, such as the top face, bottom face, and lateral face of the housing 41a, and the power receiving terminals 15a, 15b, etc. are connected to the power receiving part 16 in the ultrasound probe 41, respectively. The other internal configuration of the ultrasound probe 41 is the same as that of the ultrasound probe 1 in Embodiment 1.

Since the plurality of power receiving terminals 15a, 15b, etc. is disposed at mutually different positions of the housing 41a, an operator can appropriately connect the power supply terminal 31 of the glove 34 to a power receiving terminal that is most easily connected according to a method of gripping the ultrasound probe 41, and the operativity of the ultrasound probe 41 can be improved while performing power supply.

In addition, in this case, it is preferable that the plurality of power receiving terminals 15a, 15b, etc. has unique IDs, respectively, in advance and power supply is started after a power receiving terminal is specified by reading the ID of a power receiving terminal to which the power supply terminal 31 is connected among the plurality of power receiving terminals 15a, 15b, etc.

Embodiment 3

Figure 6:
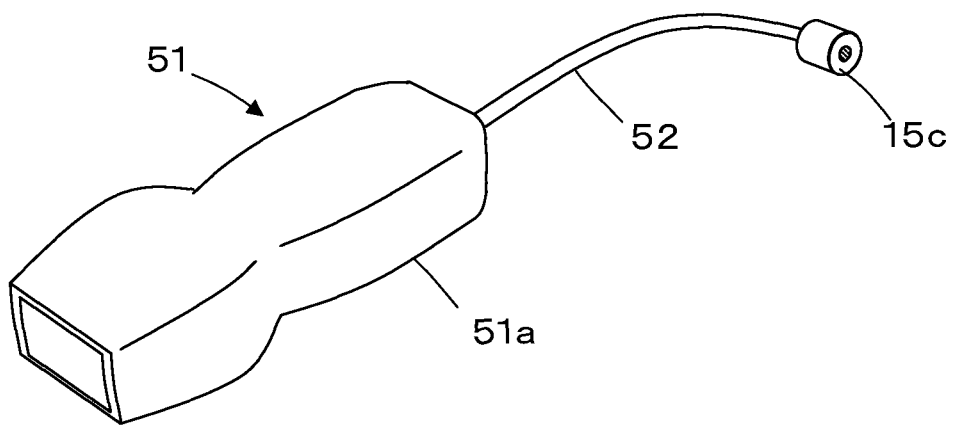
FIG. 6 is a perspective view showing an ultrasound probe in Embodiment 3.

FIG. 6 shows an ultrasound probe 51 related to Embodiment 3. The ultrasound probe 51 has a flexible cable 52 for power reception pulled out to the outside from the housing 51a, and a power receiving terminal 15c is arranged at a distal end of the cable 52 for power reception. The power receiving terminal 15c is connected to the power receiving part 16 in the ultrasound probe 51 via the cable 52 for power reception. In addition, in other respects, the internal configuration of the ultrasound probe 51 is the same as that of the ultrasound probe 1 in Embodiment 1.

By arranging the power receiving terminal 15c at the distal end of the flexible cable 52 for power reception pulled out to the outside from the housing 51a, the power receiving terminal 15c can be located in a free position and orientation with respect to the housing 51a of the ultrasound probe 51, and it is possible to further improve the operativity of the ultrasound probe 51 while performing power supply.

In this case, the power supply terminal 31 connected to the power receiving terminal 15c may be attached to the glove 34 as shown in FIG. 3, or can also be attached to a wristband that an operator wears on his/her hand.

Embodiment 4

Figure 7:
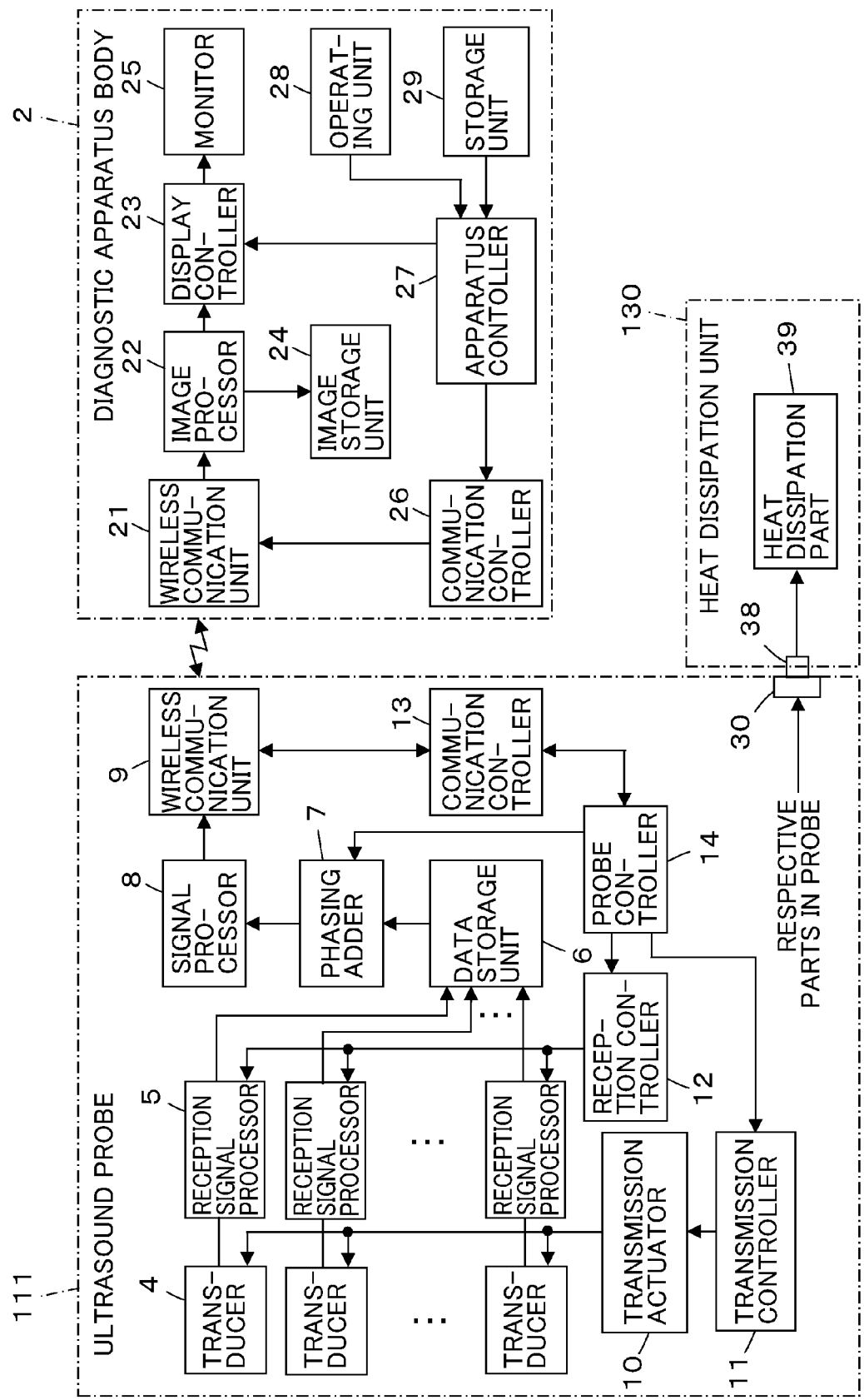
FIG. 7 is a block diagram showing the configuration of an ultrasound diagnostic apparatus related to Embodiment 4.

FIG. 7 shows the configuration of an ultrasound diagnostic apparatus related to Embodiment 4 of the invention. The ultrasound diagnostic apparatus includes an ultrasound probe 111, the diagnostic apparatus body 2 connected to the ultrasound probe 111 by wireless communication, and a heat dissipation unit 130 detachably connected to the ultrasound probe 111.

The diagnostic apparatus body 2 is the same as the diagnostic apparatus body used for the ultrasound diagnostic apparatus of Embodiment 1 shown in FIG. 1.

In the ultrasound probe 111, a heat dissipation terminal 30 thermally connected to the respective parts that generate heat in the ultrasound probe 111 is disposed instead of the power receiving terminal 15 and the power receiving part 16 in the ultrasound probe 1 of Embodiment 1 shown in FIG. 1, and the other members and the functions thereof are the same as those of the ultrasound probe 1.

The heat dissipation unit 130 is provided to dissipate the heat generated within the ultrasound probe 111, and has a heat receiving terminal 38 detachably connected to the heat dissipation terminal 30 of the ultrasound probe 111, and a heat dissipation part 39 thermally connected to the heat receiving terminal 38.

Figure 8:
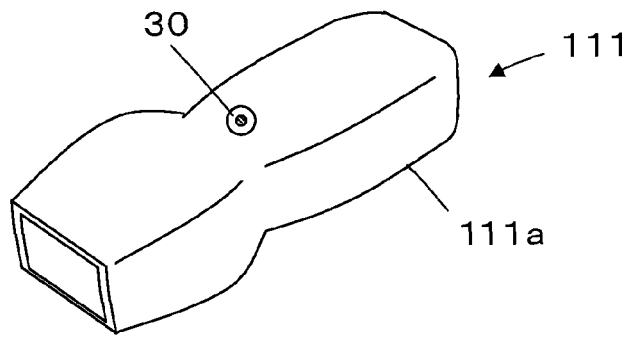
FIG. 8 is a perspective view showing an ultrasound probe in Embodiment 4.

As shown in FIG. 8, the heat dissipation terminal 30 is disposed at a housing 111a of the ultrasound probe 111 so as to be exposed to the outside, and is thermally connected to the respective parts that generate heat in the ultrasound probe 111 via a heat transfer member having excellent thermal conductivity, such as Cu or Al, for example, the plurality of reception signal processors 5, the phasing adder 7, the signal processor 8, and the like.

Figure 9:
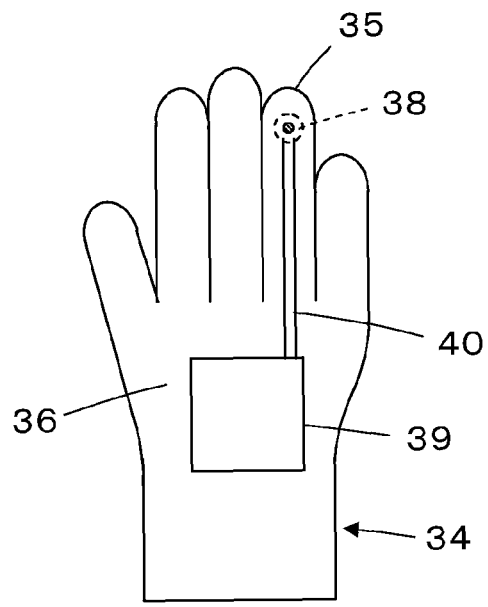
FIG. 9 is a view showing a glove to which a heat dissipation unit is attached in Embodiment 4.

On the other hand, as shown in FIG. 9, the heat dissipation unit 130 is attached to the glove 34 worn on an operator's hand. For example, while the heat receiving terminal 38 is formed on the ventral side of the finger part 35 of a glove 34 so as to protrude therefrom, a heat sink as a heat dissipation part 39 is mounted on the back part 36 of the glove 34, and the heat receiving terminal 38 and the heat dissipation part 39 are connected together via a heat transfer member 40 having excellent thermal conductivity, such as Cu or Al.

Next, the operation of Embodiment 4 will be described.

Figure 10:
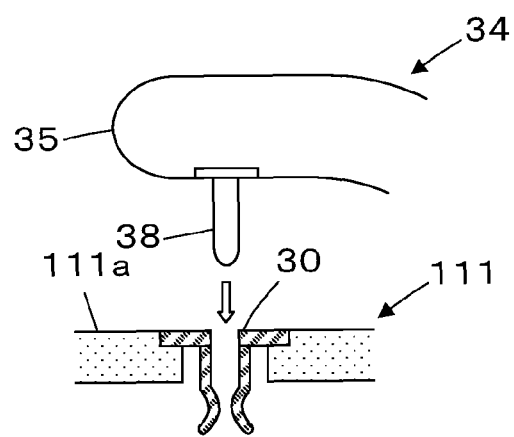
FIG. 10 is a view showing a heat dissipation terminal and a heat receiving terminal in Embodiment 4.

First, as shown in FIG. 10, an operator wears the glove 34 on his/her hand, and grips the housing 111a of the ultrasound probe 111 in a state where the heat receiving terminal 38 formed on the finger part 35 of the glove 34 so as to protrude therefrom is pressed against and fitted to the heat dissipation terminal 30 of the ultrasound probe 111, whereby the heat receiving terminal 38 and the heat dissipation terminal 30 are connected to each other. Thereby, the respective parts, such as the plurality of reception signal processors 5, the phasing adder 7, and the signal processor 8, which generate heat in the ultrasound probe 111, are thermally connected to the heat dissipation part 39 via the heat dissipation terminal 30, the heat receiving terminal 38, and the heat transfer member 40.

Diagnosis is started in this state. That is, ultrasonic waves are transmitted from the plurality of transducers 4 that constitutes the transducer array according to actuation signals supplied from the transmission actuator 10 of the ultrasound probe 111, reception signals output from the respective transducers 4 that have received ultrasonic echoes from a subject are supplied to the corresponding reception signal processors 5, respectively, to generate sample data, sound ray signals are generated in the phasing adder 7, and then, B mode image signals generated in the signal processor 8 are wirelessly transmitted to the diagnostic apparatus body 2 from the wireless communication unit 9. The B mode image signals received in the wireless communication unit 21 of the diagnostic apparatus body 2 are subjected to image processing, such as gradation processing, in the image processor 22, and then, an ultrasound diagnostic image is displayed on the monitor 25 by the display controller 23, on the basis of the B mode image signals.

When such diagnosis is performed, in the ultrasound probe 111, heat is generated mainly from the plurality of reception signal processors 5, the phasing adder 7, the signal processor 8, and the like with the processing of signals. However, these heat generating parts are thermally connected to the heat dissipation terminal 30 via the heat transfer member in the ultrasound probe 111 and are thermally connected to the heat dissipation part 39 via the heat receiving terminal 38 and the heat transfer member 40. Therefore, the heat generated within the ultrasound probe 111 is conducted to the heat dissipation part 39 of the glove 34 that the operator wears on his/her hand via the heat transfer member, the heat dissipation terminal 30, the heat receiving terminal 38, and the heat transfer member 40 in the ultrasound probe 111 from the respective heat generating parts, and is released into the atmosphere from the heat dissipation part 39.

Accordingly, a temperature rise in the ultrasound probe 111 can be efficiently suppressed, and it is possible to obtain a high-precision ultrasound image.

In addition, the heat receiving terminal 38 is preferably arranged at the finger part 35, such as the ring finger and little finger of the glove 34, or can also be arranged on the palm of the glove 34 so that the operation of the ultrasound probe 111 is not damaged. Additionally, it is preferable to select the arrangement position of the heat dissipation terminal 30 in the housing 111a of the ultrasound probe so that an operator may easily grip the ultrasound probe 111 according to the arrangement position of the heat receiving terminal 38 in the glove 34.

Although the heat dissipation terminal 30 is disposed at the housing 111a of the ultrasound probe 111 so as to be exposed to the outside, when an openable and closable lid is formed so as not to connect the heat receiving terminal 38 of the glove 34, the heat dissipation terminal can also be configured so as not to be touched by an operator's hand or finger from the outside. If such a lid is formed, a possibility that the heat dissipation terminal 30 may be damaged due to dust or the like is reduced.

Embodiment 5

Figure 11:
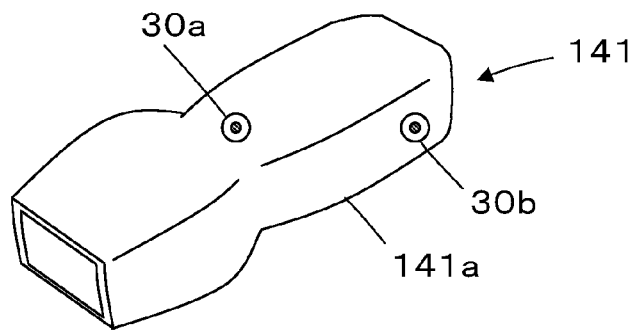
FIG. 11 is a perspective view showing an ultrasound probe in Embodiment 5.

FIG. 11 shows an ultrasound probe 141 related to Embodiment 5. The ultrasound probe 141 has a plurality of heat dissipation terminals 30a, 30b, etc. at mutually different positions, such as the top face, bottom face, and lateral face of a housing 141a, and the heat dissipation terminals 30a, 30b, etc. are thermally connected to the respective parts that generate heat in the ultrasound probe 141, respectively. The internal configuration of the ultrasound probe 141 is the same as that of the ultrasound probe 111 in Embodiment 4.

Since the plurality of heat dissipation terminals 30a, 30b, etc. is disposed at mutually different positions of the housing 141a, an operator can appropriately connect the heat receiving terminal 38 of the glove 34 to a heat dissipation terminal that is most easily connected according to a method of gripping the ultrasound probe 141, and the operativity of the ultrasound probe 141 can be improved while performing heat dissipation.

Embodiment 6

Figure 12:
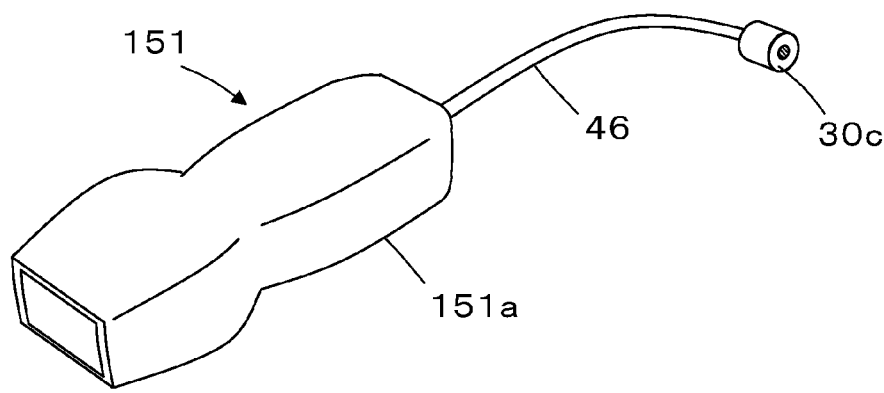
FIG. 12 is a perspective view showing an ultrasound probe in Embodiment 6.

FIG. 12 shows an ultrasound probe 151 related to Embodiment 6. The ultrasound probe 151 has a flexible cable 46 for heat dissipation pulled out to the outside from a housing 151a, and a heat dissipation terminal 30c is arranged at a distal end of the cable 46 for heat dissipation. The heat dissipation terminal 30c is thermally connected to the respective parts that generate heat in the ultrasound probe 151 via the cable 46 for heat dissipation. In addition, the internal configuration of the ultrasound probe 151 is the same as that of the ultrasound probe 111 in Embodiment 4.

By arranging the heat dissipation terminal 30c at the distal end of the flexible cable 46 for heat dissipation pulled out to the outside from the housing 151a, the heat dissipation terminal 30c can be located in a free position and orientation with respect to the housing 151a of the ultrasound probe 151, and it is possible to further improve the operativity of the ultrasound probe 151 while performing heat dissipation.

In this case, the heat receiving terminal 38 connected to the heat dissipation terminal 30c may be attached to the glove 34 as shown in FIG. 9, or can also be attached to a wristband that an operator wears on his/her hand.

Embodiment 7

Figure 13:
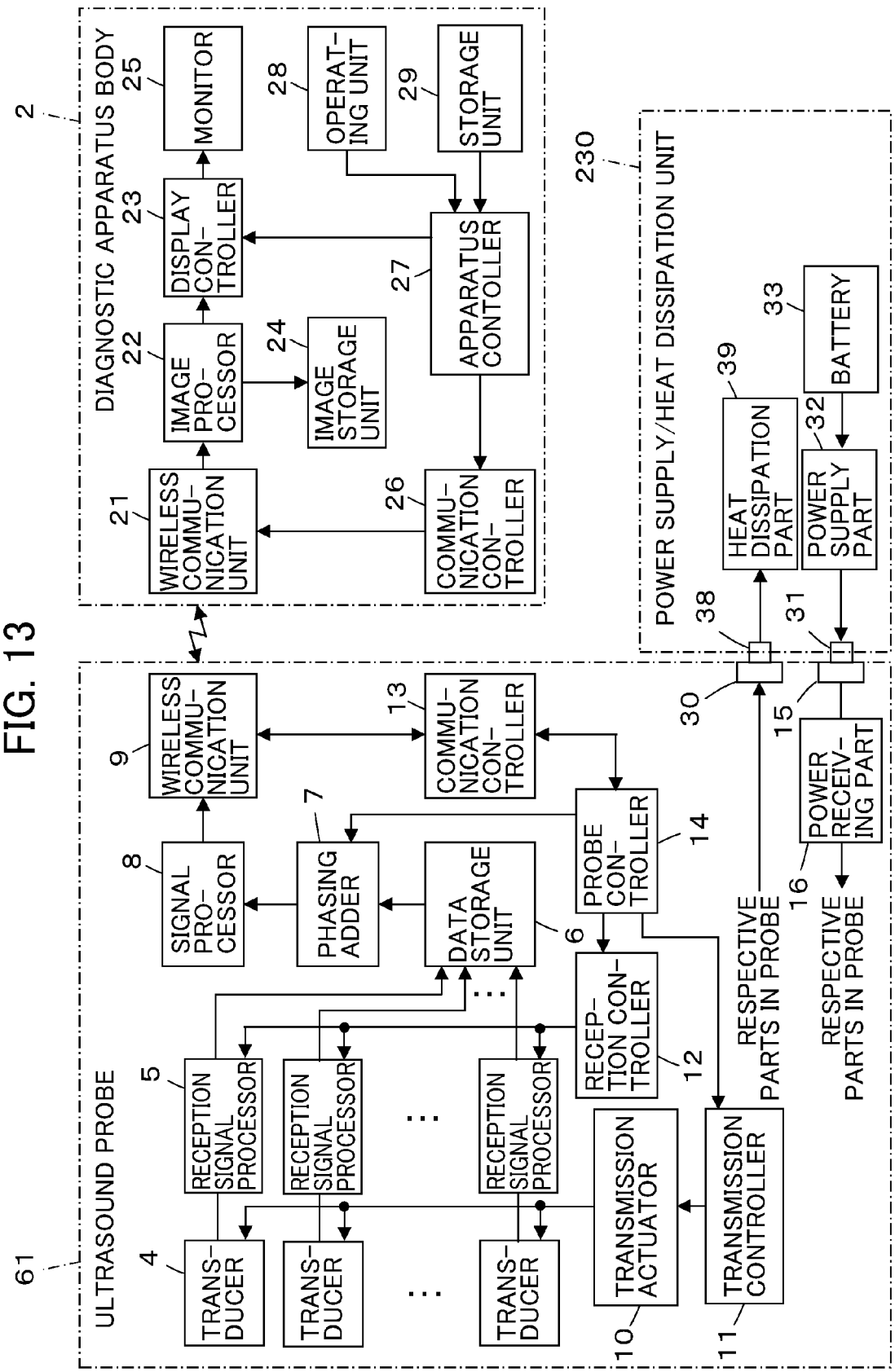
FIG. 13 is a block diagram showing the configuration of an ultrasound diagnostic apparatus related to Embodiment 7.

FIG. 13 shows the configuration of an ultrasound diagnostic apparatus related to Embodiment 7. This ultrasound diagnostic apparatus includes an ultrasound probe 61 connected to the diagnostic apparatus body 2 by wireless communication, and a power supply/heat dissipation unit 230 detachably connected to the ultrasound probe 61.

The ultrasound probe 61 further includes the power receiving terminal 15 disposed at a housing of the ultrasound probe 61 so as to be exposed to the outside, and the power receiving part 16 electrically connected to the power receiving terminal 15, in the ultrasound probe 111 in Embodiment 4 shown in FIG. 7, and the other members and the function thereof are the same as those of the ultrasound probe 111.

The power receiving part 16 is the same as that of the power receiving part in Embodiment 1 shown in FIG. 1, and is provided to supply electric power to the respective parts that require electric power in the ultrasound probe 61.

The power supply/heat dissipation unit 230 further includes the power supply terminal 31 detachably connected to the power receiving terminal 15 of the ultrasound probe 61, the power supply part 32 electrically connected to the power supply terminal 31, and the battery 33 electrically connected to the power supply part 32, in the heat dissipation unit 130 in Embodiment 4 shown in FIG. 7.

The power supply terminal 31, the power supply part 32, and the battery 33 are the same as those of the power supply terminal, the power supply part, and the battery in Embodiment 1 shown in FIG. 1, and the power supply part 32 is provided to supply the electric power from the battery 33 to the power receiving part 16 of the ultrasound probe 61 via the power supply terminal 31 and the power receiving terminal 15 of the ultrasound probe 61.

The power supply terminal 31 can be attached to the glove 34 shown in FIG. 9 along with the heat receiving terminal 15, or can also be attached to a wristband that an operator wears on his/her hand.

When diagnosis is performed, an operator presses and fits the heat receiving terminal 38 and the power supply terminal 31 of the power supply/heat dissipation unit 230 against/to the heat dissipation terminal 30 and the power receiving terminal 15 of the ultrasound probe 61, respectively, to connect the heat receiving terminal 38 and the heat dissipation terminal 30 to each other and connect the power supply terminal 31 and the power receiving terminal 15 to each other. Thereby, the battery 33 in the power supply/heat dissipation unit 230 is electrically connected to the power receiving part 16 via the power supply part 32, the power supply terminal 31, and the power receiving terminal 15 of the ultrasound probe 61, the electric power from the battery 33 is supplied to the respective parts in the ultrasound probe 61, whereby diagnosis is performed.

At this time, the heat generated within the ultrasound probe 61 is conducted to the heat dissipation part 39 of the glove 34 via the heat transfer member, the heat dissipation terminal 30, the heat receiving terminal 38, and the heat transfer member 40 in the ultrasound probe 61 from the respective heat generating parts, and is released into the atmosphere from the heat dissipation part 39.

For this reason, ultrasonic diagnosis can be performed while performing supply of electric power to the respective parts in the ultrasound probe 61 and suppressing a temperature rise in the ultrasound probe 61.

Figure 14:
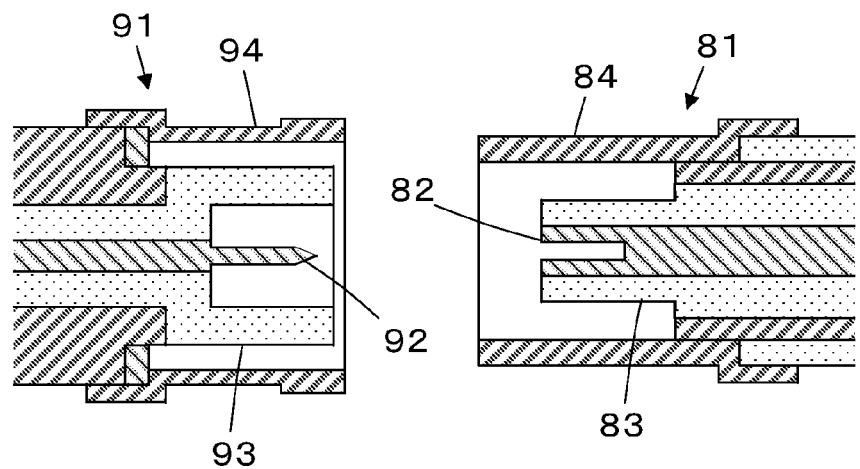
FIG. 14 is a cross-sectional view showing a coaxial connector used in a modification of Embodiment 7.

Additionally, the heat dissipation terminal 30 and the power receiving terminal 15 of the ultrasound probe 61 can also be formed in a single connector. For example, a receptacle 81 of a coaxial connector as shown in FIG. 14 is attached to the housing of the ultrasound probe 61 and a central contact 82 is electrically connected to the power receiving part 16 so as to be used as the power receiving terminal 15, and an external contact 84 insulated from the central contact 82 by an insulator 83 is thermally connected to the respective parts that generate heat in the ultrasound probe 61 so as to be used as the heat dissipation terminal 30.

On the other hand, a plug 91 to fit to the receptacle 81 is attached to the glove 34 worn on an operator's hand and a central contact 92 is electrically connected to the power supply part 32 so as to be used as the power supply terminal 31, and an external contact 94 insulated from the central contact 92 by an insulator 93 is thermally connected to the heat dissipation part 39 so as to be used as the heat receiving terminal 38.

Since such a coaxial connector is used, the heat receiving terminal 38 and the power supply terminal 31 of the power supply/heat dissipation unit 230 can be connected to the heat dissipation terminal 30 and the power receiving terminal 15 of the ultrasound probe 61, respectively, simply by fitting the plug 91 attached to the glove 34 to the receptacle 81 attached to the housing of the ultrasound probe 61, whereby workability is improved.

In addition, the receptacle 81 of the coaxial connector is attached to the housing of the ultrasound probe 61 and the plug 91 is attached to the glove 34. On the contrary, however, a plug in which the heat dissipation terminal 30 and the power receiving terminal 15 are formed may be attached to the housing of the ultrasound probe 61, and a receptacle in which the heat receiving terminal 38 and the power supply terminal 31 are formed may be attached to the glove 34.

Similarly to the above-described Embodiments 2 and 5, it is possible to adopt a configuration in which a plurality of the receptacles 81 in which the heat dissipation terminal 30 and the power receiving terminal 15 are formed, respectively, are disposed in the housing of the ultrasound probe 61, and the plug 91 of a glove 34 is connected to a receptacle 81 that is most easily connected according to a method of gripping the ultrasound probe 61. In this way, the operativity of the ultrasound probe 61 can be improved while performing heat dissipation and power supply.

In addition, in this case, it is preferable that the plurality of receptacles 81 has unique IDs, respectively, in advance and power supply is started after a receptacle 81 is specified by reading the ID of a receptacle 81 to which the plug 91 is connected among the plurality of receptacles 81.

Additionally, similarly to the above-described Embodiments 3 and 6, the flexible cable can be pulled out to the outside from the housing of the ultrasound probe 61, and the receptacle 81 can also be arranged at the distal end of this cable. If such a configuration is adopted, the operativity of the ultrasound probe 61 is further improved.

In the above-described embodiments 4 to 7, the ultrasound probe 111 or 61 and the diagnostic apparatus body 2 are connected to each other by wireless communication. However, the invention is not limited thereto, and the ultrasound probe 111 or 61 may be connected to the diagnostic apparatus body 2 via a connecting cable. In this case, the wireless communication unit 9 and the communication controller 13 of the ultrasound probe 111 or 61, the wireless communication unit 21 and communication controller 26 of the diagnostic apparatus body 2, and the like become unnecessary.

In the above-described Embodiments 1 to 3 and 7, the electric power received in the power receiving part 16 is directly supplied to the respective parts in the ultrasound probe 1 or 61. The invention is not limited thereto. It is possible to adopt a configuration in which a battery is built in advance in the ultrasound probe 1, electric power is supplied to the built-in battery of the ultrasound probe 1 or 61 from the power receiving part 16, and electric power is supplied to the respective parts in the ultrasound probe 1 or 61 from this battery.

Embodiment 8

Figure 15:
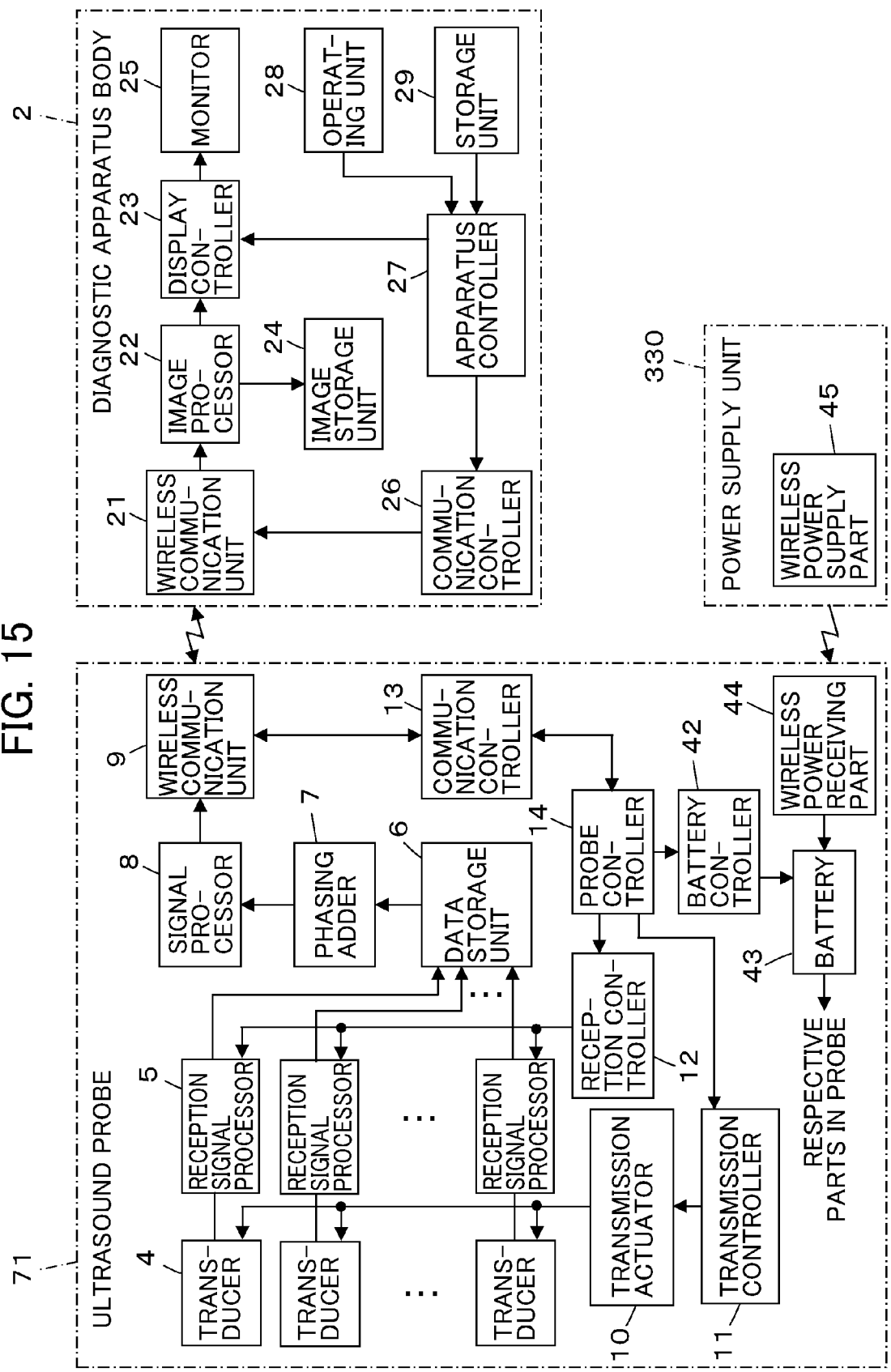
FIG. 15 is a block diagram showing the configuration of an ultrasound diagnostic apparatus related to Embodiment 8.

FIG. 15 shows the configuration of an ultrasound diagnostic apparatus related to Embodiment 8 of the invention. The ultrasound diagnostic apparatus includes an ultrasound probe 71, the diagnostic apparatus body 2 connected to the ultrasound probe 71 by wireless communication, and a power supply unit 330 that performs wireless power supply to the ultrasound probe 71.

The diagnostic apparatus body 2 is the same as the diagnostic apparatus body used for the ultrasound diagnostic apparatus of Embodiment 1 shown in FIG. 1.

The ultrasound probe 71 includes a battery controller 42, a battery 43, and a wireless power receiving part 44 instead of the power receiving terminal 15 and the power receiving part 16, in the ultrasound probe 1 shown in FIG. 1, and the other components are the same as those of the ultrasound probe 1 used in Embodiment 1.

The battery 43 is connected to the probe controller 14 of the ultrasound probe 71 via the battery controller 42, and a wireless power receiving part 44 for charging is connected to the battery 43.

The battery 43 functions as a power source of the ultrasound probe 71, and supplies electric power to the respective parts that require electric power in the ultrasound probe 71. The battery controller 42 controls the supply of electric power from the battery 43 to the respective parts in the ultrasound probe 71, monitors the amount of electric power remaining in the battery 43, and controls the wireless-charging of the battery 43 from the power supply unit 330 via the wireless power receiving part 44.

The power supply unit 330 has a wireless power supply part 45, and if the battery controller 42 in the ultrasound probe 71 determines that the amount of electric power remaining in the battery 43 has fallen below a preset threshold, electric power is supplied to the wireless power receiving part 44 of the ultrasound probe 71 from the wireless power supply part 45 in a non-contact manner by electromagnetic induction or the like, and a charging operation of the battery 43 is executed.

Figure 16:
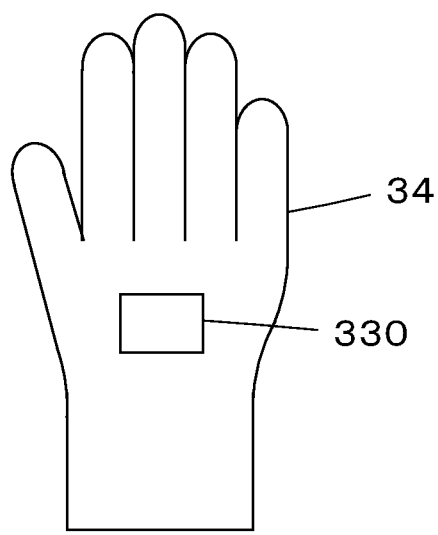
FIG. 16 is a view showing a glove to which a power supply unit is attached in Embodiment 8.

Additionally, the power supply unit 330, as shown in FIG. 16, is attached to the back part of the glove 34 worn on an operator's hand. Accordingly, since the distance between the wireless power receiving part 44 and the wireless power supply part 45 shortens if the ultrasound probe 71 is gripped by the hand on which the glove 34 is worn, electric power can be stably supplied to the battery 43 from the wireless power supply part 45 without being influenced by a gripping method of the ultrasound probe 71 by an operator, and other instruments around a position where the operator stands and the ultrasound diagnostic apparatus.

Additionally the operator can perform an operation without the problems of a cable compared to an ultrasound probe using a cable. Moreover, since it is possible to supply electric power even while the ultrasound probe 71 is used, even if the battery 43 is enlarged, the ultrasound probe 71 can also be used at any time.

Figure 17:
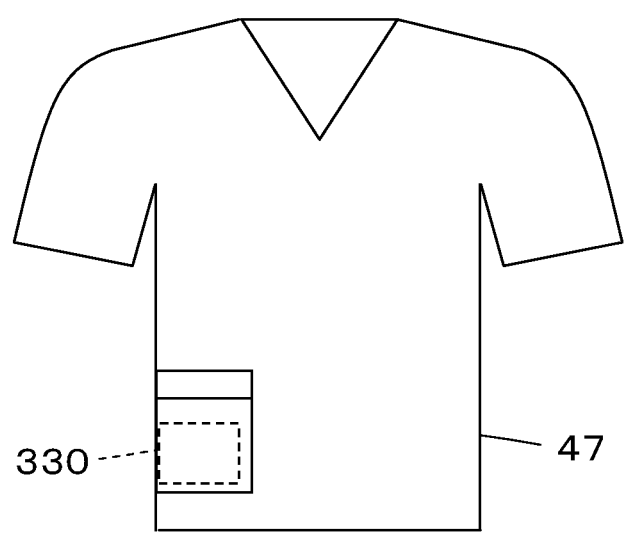
FIG. 17 is a view showing a jacket to which the power supply unit used in Embodiment 8 is attached.

In addition, in Embodiment 8, the power supply unit 330 is attached to the glove 34 worn on an operator's hand. However, the invention is not limited to this if attachment to an operator's body is possible. As shown in FIG. 17, the power supply unit 330 may be attached to a jacket 47 worn by the operator, for example, in a pocket.

Embodiment 9

Figure 18:
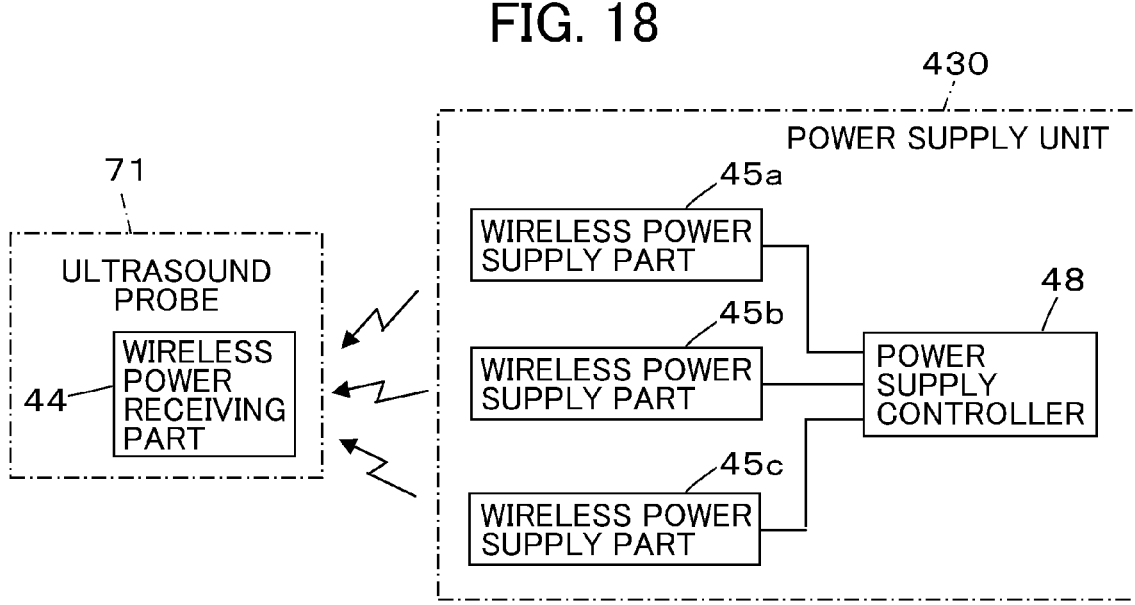
FIG. 18 is a block diagram showing the power supply unit used in Embodiment 9.

A power supply unit 430 as shown in FIG. 18 can also be used instead of the power supply unit 330 of the ultrasound diagnostic apparatus related to Embodiment 8.

Figure 19:
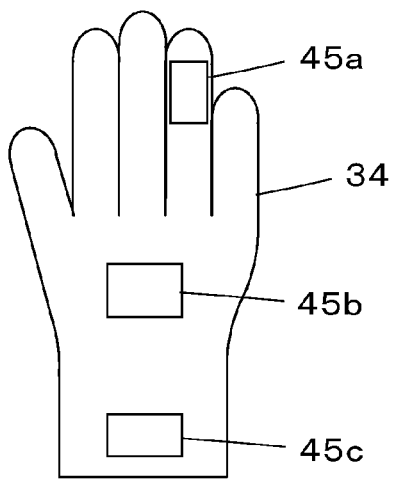
FIG. 19 is a view showing a jacket to which the power supply unit used in Embodiment 9 is attached.

The power supply unit 430 includes a plurality of wireless power supply parts 45a to 45c, which are connected to a power supply controller 48, respectively. The plurality of wireless power supply parts 45a to 45c, as shown in FIG. 19, is provided, for example, at the fingertip, back, and wrist of the glove 34, respectively.

The power supply controller 48 selects a wireless power supply part that is capable of charging the wireless power receiving part 44, is nearest thereto and has high power supply efficiency, with the ultrasound probe 71 being gripped by a hand on which an operator wears the glove 34, among the plurality of wireless power supply parts 45a to 45c if necessary on the basis of the amount of electric power remaining in the battery 43 transmitted by wireless communication from the ultrasound probe 71, performs wireless power transmission to the wireless power receiving part 44, and makes the battery 43 supply electric power.

If such a power supply unit 430 is provided, the distance between the wireless power receiving part 44 and the wireless power supply part 45 shortens, the wireless power supply parts 45a to 45c are arranged in a plurality of directions with respect to the wireless power receiving part 44, and a wireless power supply part suitable for a gripping method of the ultrasound probe by an operator is selected from the plurality of wireless power supply parts 45, whereby a power supply operation is performed. Therefore, the stable supply of electric power to the battery 43 of the ultrasound probe 71 can be performed without being influenced by the operator's gripping method.

Embodiment 10

Figure 20:
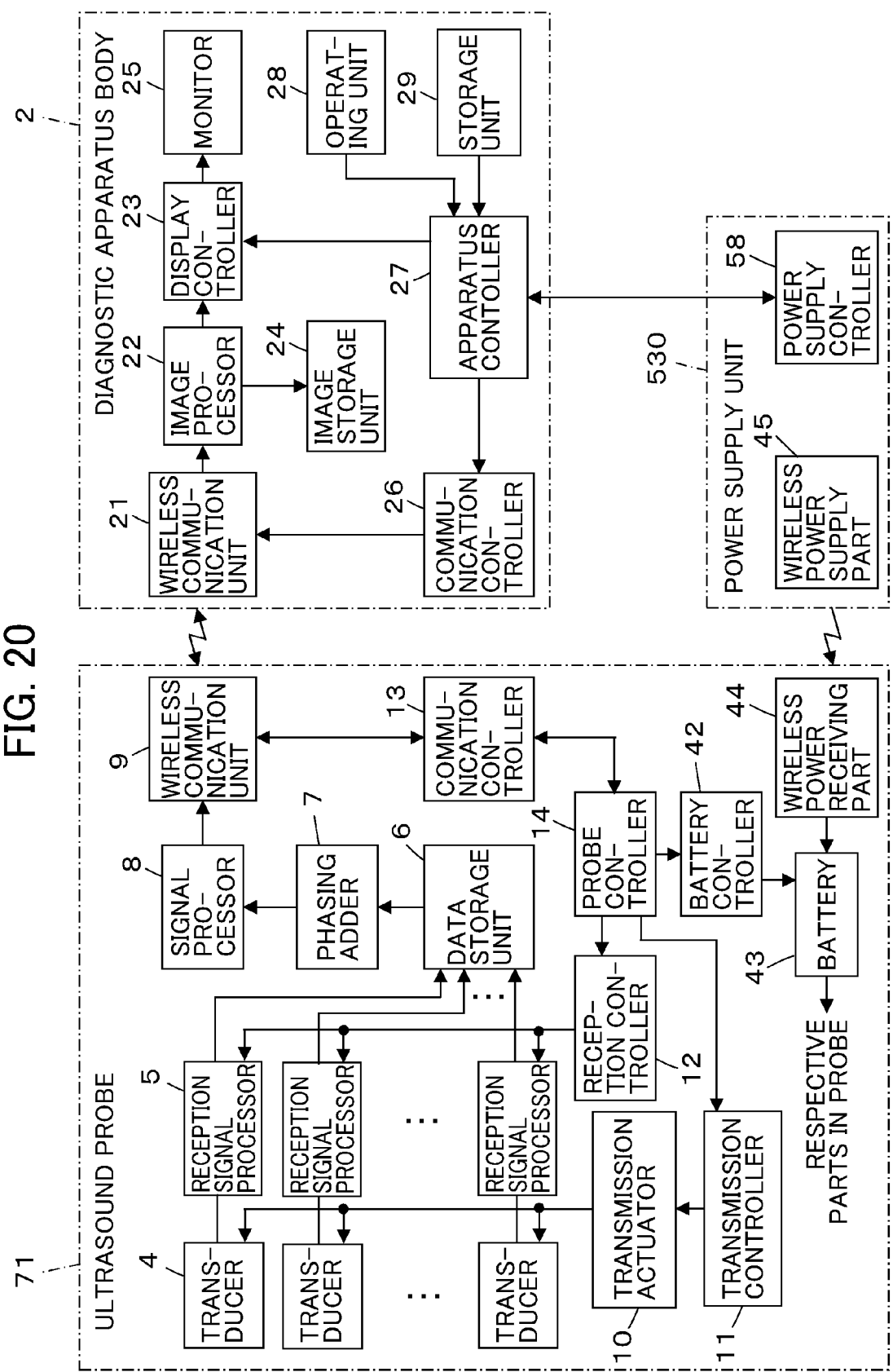
FIG. 20 is a block diagram showing the configuration of an ultrasound diagnostic apparatus related to Embodiment 10.

FIG. 20 shows the configuration of an ultrasound diagnostic apparatus related to Embodiment 10. The ultrasound diagnostic apparatus includes the ultrasound probe 71, the diagnostic apparatus body 2 connected to the ultrasound probe 71 by wireless communication, and a power supply unit 530 that performs wireless power supply to the ultrasound probe 1.

The ultrasound probe 71 is the same as the ultrasound probe used for the ultrasound diagnostic apparatus of Embodiment 8 shown in FIG. 15. Additionally, although the diagnostic apparatus body 2 is different from the diagnostic apparatus body used for the ultrasound diagnostic apparatus of Embodiment 1 shown in FIG. 1 in terms of the functions of the operating unit 28 and the apparatus controller 27, the other components and the functions thereof are the same.

The operating unit 28 of the diagnostic apparatus body 2 constitutes the selecting means of the invention, and has the function of allowing an operator to select the alternatives of a first mode in which transmission and reception of ultrasonic waves is performed by the transducer array of the ultrasound probe 71 while performing power supply to the battery 43 by the wireless power supply part 45, and a second mode in which power supply is stopped by wireless power supply part 45 to perform the transmission and reception of ultrasonic waves by the transducer array of the ultrasound probe 71.

The apparatus controller 27 controls the power supply controller 58 on the basis of the first mode or the second mode selected by the operator, in the operating unit 28. That is, in a case where the first mode is selected, the power supply controller 58 is controlled so as to perform power supply to the battery 43 via the wireless power receiving part 44 by the wireless power supply part 45 irrespective of the transmission and reception of ultrasonic waves by the transducer array of the ultrasound probe 1, and in a case where the second mode is selected, the power supply controller 58 is controlled so as to stop the power supply to the battery 43 via the wireless power receiving part 44 by the wireless power supply part 45 when the transmission and reception of ultrasonic waves by the transducer array of the ultrasound probe 71.

The power supply unit 530 further includes a power supply controller 58 connected to the apparatus controller 27 of the diagnostic apparatus body 2, in the power supply unit 330 of Embodiment 8 shown in FIG. 15, and the other components and the functions thereof are the same as those of the power supply unit 330 of Embodiment 8.

The wireless power supply part 45 that performs power supply to the wireless power receiving part 44 built in the ultrasound probe 71 is connected to the power supply controller 58.

The power supply controller 58 supplies electric power to the wireless power receiving part 44 of the ultrasound probe 71 from the wireless power supply part 45 in a non-contact manner by electromagnetic induction or the like under the control of the apparatus controller 27, thereby executing a charging operation of the battery 43.

In the first mode, the charging of the battery 43 and the transmission and reception of the ultrasonic wave by the transducer array are simultaneously performed. Therefore, there is a possibility that image quality may deteriorate under the influence of a strong magnetic field that a weak reception signal output from each transducer 4 of the transducer array generates from the wireless power supply part 45. However, in the case of the diagnosis that does not require high image quality, the ultrasound probe can be used without suspending the operation.

On the other hand, in the second mode, the charging of the battery 43 is stopped when the transmission and reception of ultrasonic waves by the transducer array are performed. Thus, a high image-quality ultrasound image can be acquired without being influenced by a strong magnetic field that a weak reception signal output from each transducer 4 of the transducer array generates from the wireless power supply part 45.

By selecting two such modes, the prolonged continuous running of the ultrasound diagnostic apparatus, and a high image-quality ultrasound image can be obtained if required for diagnosis.

Next, the operation of Embodiment 10 will be described.

When diagnosis is performed, ultrasonic waves are transmitted from the plurality of transducers 4 according to actuation signals supplied from the transmission actuator 10 of the ultrasound probe 71, reception signals output from the respective transducers 4 that have received ultrasonic echoes from a subject are supplied to the corresponding reception signal processors 5, respectively, to generate sample data, sound ray signals are generated in the phasing adder 7, and then, B mode image signals generated in the signal processor 8 are wirelessly transmitted to the diagnostic apparatus body 2 from the wireless communication unit 9. The B mode image signals received in the wireless communication unit 21 of the diagnostic apparatus body 2 are subjected to image processing, such as gradation processing, in the image processor 22, and then, an ultrasound diagnostic image is displayed on the monitor 25 by the display controller 23, on the basis of the B mode image signals.

Thus, although an ultrasonic diagnosis is performed in this way, when selection of the aforementioned the first mode and the second mode is performed by an operator in the operating unit 28, the apparatus controller 27 of the diagnostic apparatus body 2 determines the selected mode, and makes the battery 43 of the ultrasound probe 71 perform power supply via the power supply controller 58 of the power supply unit 530 from the wireless power supply part 45 if necessary.

The power supply unit 530, similarly to the power supply unit 330 of Embodiment 8 shown in FIG. 16, may be attached to the back part of the glove 34 worn on an operator's hand, or can also be attached to the jacket 47 that an operator wears as shown in FIG. 17, for example, in a pocket.

Embodiment 11

Figure 21:
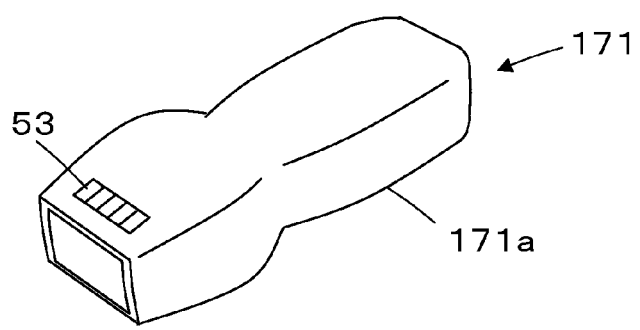
FIG. 21 is a perspective view showing an ultrasound probe in Embodiment 11.

The housing of the ultrasound probe 71 of the ultrasound diagnostic apparatus related to the above-described Embodiments 8 to 10 can be equipped with an indicator that indicates the power supply efficiency by the wireless power receiving part 17. An ultrasound probe 171 shown in FIG. 21 has an indicator 53 including a plurality of lamps in which the number of lamps to be turned on changes in stages according to the amount of electric power remaining in the battery 43. The indicator 53 is attached to the position of a housing 171*a* that can visually recognize the monitor even if an operator grips the ultrasound probe 171. If an ultrasound diagnostic apparatus having such an ultrasound probe 34 is used, an operator can appropriately check the amount of electric power remaining in the battery 43 and whether power supply is efficiently performed while performing diagnoses.

In addition, the indicator that indicates the power supply efficiency is not limited to this, an indicator that indicates the amount of electric power remaining in the battery 43 numerically and an indicator that indicates that power supply is performed by blinking of a lamp may be used.

In addition, in the ultrasound diagnostic apparatus related to the above-described Embodiments 8 to 11, the ultrasound probe 71 or 171 preferably has a housing that can recognize the position of the built-in wireless power receiving part 44. The housings that can recognize the position of the wireless power receiving part 44 include a transparent housing that allows the wireless power receiving part 44 to be visually recognized directly from the outside, housings with codes that can recognize the position of the wireless power receiving part, and the like. If such an ultrasound probe 71 or 171 is used, since the wireless power supply part(s) 45 or 45*a* to 45*c* in the power supply unit 330, 430, or 530 can be easily brought close to the wireless power receiving part 44, the supply of electric power can be efficiently and stably performed.

Additionally in the ultrasound diagnostic apparatuses related to the above-described Embodiments 8, 9, and 11, the wireless power supply parts 45 and 45*a* to 45*c* preferably stop power supply during the reception of ultrasonic echoes by the ultrasound probe 71. If wireless power supply is performed in this way, the noise produced in a weak electrical signal by an ultrasonic wave under the influence of a strong magnetic field generated from the wireless power supply part 45 can be suppressed.

Moreover, the wireless power supply part(s) 45 or 45*a* to 45*c* preferably stops the power supply during the wireless communication between the ultrasound probe 71 and the diagnostic apparatus body 2. If such wireless power supply is performed, the noise produced in the weak image signal transmitted from the wireless communication unit 9 under the influence of the strong magnetic field generated from the wireless power supply part 45 can be suppressed, and, a decrease in the transmission speed to the diagnostic apparatus body 2 can be prevented.

What is claimed is:

1. An ultrasound diagnostic apparatus comprising:
    an ultrasound probe that has i) a transducer array transmitting an ultrasonic beam toward a subject and receiving an ultrasonic echo from the subject to output reception signals and ii) a housing;
    a diagnostic apparatus body that is connected to the ultrasound probe by wireless communication and generates an ultrasound image on the basis of the reception signals output from the transducer array;
    at least one power receiving terminal that is located on the housing of the ultrasound probe and electrically connected to respective parts in the ultrasound probe; and
    a power supply unit that is attachable to an operator's body and has i) a power supply terminal which is detachably connectable to the power receiving terminal, and ii) a power supply part which supplies power to the respective parts in the ultrasound probe via the power supply terminal and the power receiving terminal when the power supply terminal is connected to the power receiving terminal,
    wherein the power supply unit is attached to a glove for wearing on an operator's hand, and
    wherein the power receiving terminal is located on the housing such that, only when the user is wearing the glove and gripping the housing of the ultrasound probe, the power receiving terminal connects with the power supply terminal and the power supply unit powers the respective parts in the ultrasound probe via the power receiving terminal and the power supply terminal.

2. The ultrasound diagnostic apparatus according to claim 1,
    wherein a plurality of the at least one power receiving terminal is located at mutually different positions of the housing of the ultrasound probe, and
    wherein the power supply terminal is selectively connected to any one of the plurality of power receiving terminals.

3. The ultrasound diagnostic apparatus according to claim 1,
    wherein the power supply unit is attached to a glove,
    the power supply terminal is mounted on a ventral side of a finger part of the glove and protrudes from the ventral side of the finger part of the glove,
    the power supply unit comprises a battery,
    the battery of the power supply unit is mounted on a back part of the glove, and
    with the glove worn on the operator's hand with the operator gripping the housing of the ultrasound probe, the power supply terminal press fits into the power receiving terminal on the housing so that the ultrasound probe is powered by the battery via the power supply terminal and the power receiving terminal.

4. An ultrasound diagnostic apparatus, comprising:

an ultrasound probe comprised of i) a housing, ii) a power receiving terminal attached to the housing and exposed to an outside of the housing, and iii) within the housing, a power receiving part connected to the power receiving terminal, ultrasound transducers that constitute a transducer array, and a wireless communication unit connected to the transducer array, wherein the transducer array transmits an ultrasonic beam toward a subject and receives an ultrasonic echo from the subject to output reception signals;

a diagnostic apparatus body wirelessly connected to the ultrasound probe by wireless communication, wherein the diagnostic apparatus body generates an ultrasound image on a basis of the reception signals output from the transducer array;

a glove; and a power supply unit mounted to the glove, the power supply unit including a battery and a power supply terminal detachably connectable to the power receiving terminal attached to the housing of the ultrasound probe, wherein with the power supply terminal connected to the power receiving terminal, the battery of the power supply unit supplies electric power to the ultrasound probe via the power receiving terminal and the power receiving part, and wherein the power supply terminal is located on the glove such that only with the glove worn on an operator's hand with the operator gripping the housing of the ultrasound probe, the power supply terminal connects with the power receiving terminal on the housing so that the ultrasound probe is powered by the battery.

5. The ultrasound diagnostic apparatus according to claim 4, the power supply terminal is mounted on a ventral side of a finger part of the glove and protrudes from the ventral side of the finger part of the glove, the battery of the power supply unit is mounted on a back part of the glove, and with the glove worn on the operator's hand with the operator gripping the housing of the ultrasound probe, the power supply terminal press fits into the power receiving terminal on the housing so that the ultrasound probe is powered by the battery via the power supply terminal and the power receiving terminal.

* * * * *